United States Patent [19]

Hotta et al.

[11] Patent Number: 5,766,672

[45] Date of Patent: Jun. 16, 1998

[54] METHOD OF MANUFACTURING AN OXYGEN CONCENTRATION DETECTOR ELEMENT

[75] Inventors: Yasumichi Hotta, Mie-ken; Hiromi Sano, Nagoya; Namitsugu Fujii, Yokkaichi; Naoto Miwa, Tsushima, all of Japan

[73] Assignee: Nippondenso Co., Ltd., Kariya, Japan

[21] Appl. No.: 704,927

[22] Filed: Aug. 28, 1996

[30] Foreign Application Priority Data

Sep. 5, 1995 [JP] Japan ................... 7-254697

[51] Int. Cl.$^6$ ........................... B05D 5/12
[52] U.S. Cl. ................ 427/58; 427/123; 427/126.3; 427/435; 427/230; 427/437; 204/427
[58] Field of Search ............... 427/58, 125, 126.3, 427/230, 435, 437, 123; 204/421, 424, 427, 428, 429

[56] References Cited

U.S. PATENT DOCUMENTS

| 4,650,697 | 3/1987 | Kitagawa et al. | 427/125 |
| 4,956,072 | 9/1990 | Kojima et al. | 204/424 |

FOREIGN PATENT DOCUMENTS

| 3923034 | 7/1989 | Germany. |
| 4139421 | 11/1991 | Germany. |
| 182159 | 11/1982 | Japan. |
| 57-182158 | 11/1982 | Japan. |
| 59-166697 | 9/1984 | Japan. |

OTHER PUBLICATIONS

Abstract 4,229,835 dated Sep. 1992.
Abstract 4,330,749 dated Sep. 1983.

Primary Examiner—Michael Lusignan
Assistant Examiner—Brian K. Talbot
Attorney, Agent, or Firm—Cushman Darby & Cushman IP Group of Pillsbury Madison & Sutro LLP

[57] ABSTRACT

An oxygen concentration detector element 2 includes a cup-shaped solid electrolyte 20 with an inside chamber 25 opened at one end and closed at the other end. An external electrode 21 is formed on an outer surface of solid electrolyte 20 by dipping solid electrolyte 20 in first chemical plating liquid 81, while an internal electrode 22 is formed on an inner surface of solid electrolyte 20 by introducing second chemical plating liquid 82 into inside chamber 25. First, in an injecting step, an injection needle 11 is inserted into inside chamber 25 and second chemical plating liquid 82 is introduced into inside chamber 25 via injection needle 11, and then injection needle 11 is pulled out of inside chamber 25. Next, in a plating step, internal electrode 22 is formed on the inner surface of inside chamber 25 using second chemical plating liquid 82. Then, in a discharging step, residual second chemical plating liquid 82 is discharged from inside chamber 25.

6 Claims, 8 Drawing Sheets

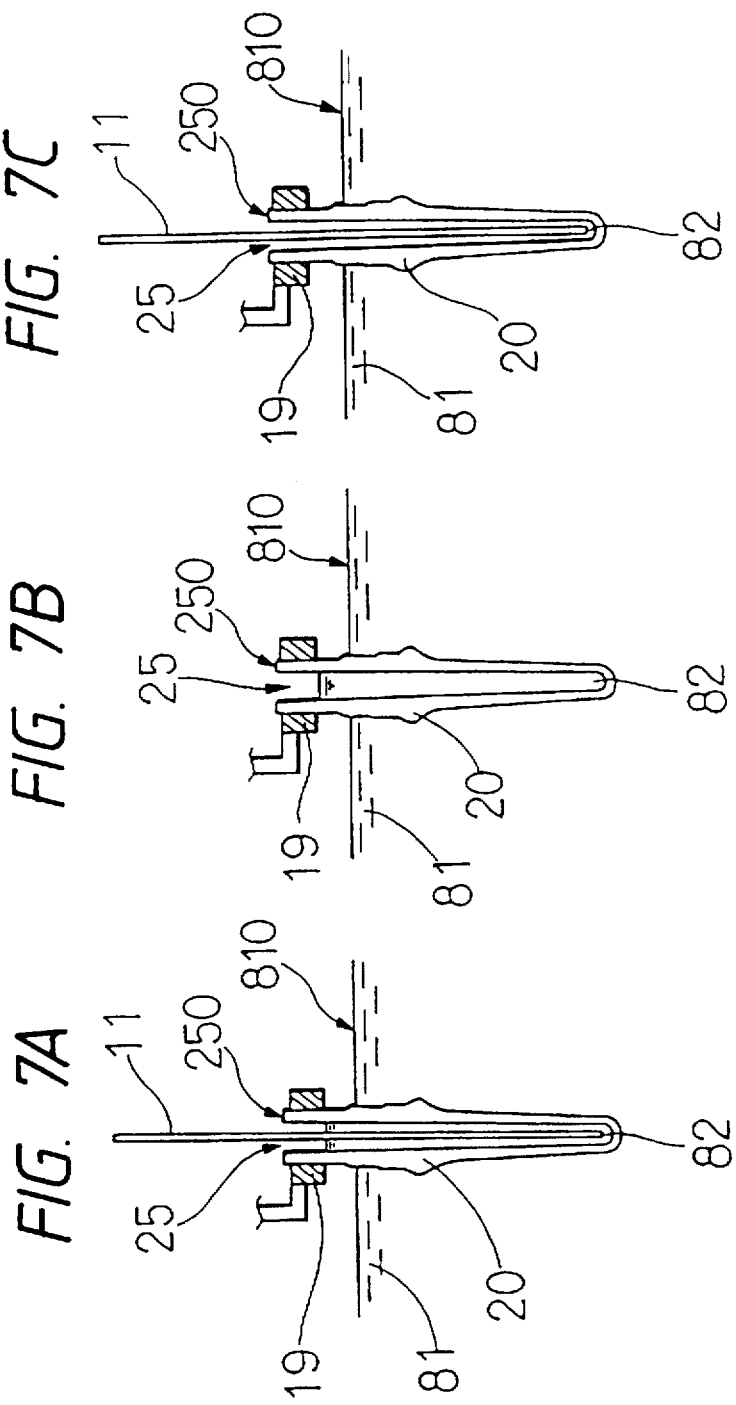

METHOD OF MANUFACTURING AN OXYGEN CONCENTRATION DETECTOR ELEMENT

BACKGROUND OF THE INVENTION

1. Field of the Invention:

This invention relates to a method of manufacturing an oxygen concentration detector element, which is preferably used to control an air-fuel ratio of an internal combustion engine of an automotive vehicle.

2. Description of the Related Art

A conventional oxygen concentration detector element such as, for example, the detector element disclosed in Japanese Patent No. HEI 2-15016, granted in 1990, comprises a cup-shaped solid electrolyte defining therein an inside chamber having one end closed and the other end opened. An external electrode is formed on an outer surface of the solid electrolyte, while an internal electrode is formed on a wall of the inside chamber. In forming these external and internal electrodes, it is generally known that the chemical plating is used.

More specifically, as shown in FIGS. 8A, 8B and 9, the chemical plating of the external and internal electrodes is performed by using a plating jig 9 as well as a plating tank 89 storing chemical plating liquid 80 therein.

Plating jig 9 is connected to an air pump 900 supplying pressurized air and comprises a main pipe 90 disposed horizontally for guiding the pressurized air supplied from air pump 900 and a plurality of branch pipes 93 communicating with and extending downward from this main pipe 90. Each branch pipe 93 has a lower end integrally connected with a cylindrical holder 92 which securely holds a solid electrolyte 20. An injection needle 91, having an opening at its distal end and communicating with an inside space of branch pipe 93 at its base end, is provided at the bottom of branch pipe 93 so as to extend downward along the axis of holder 92. Furthermore, a plurality of small holes 94 are opened in the boundary region between each branch pipe 93 and holder 92.

Solid electrolyte 20 is inserted at its top portion into a bottom ring of holder 92 and fixed there. In this case, injection needle 91 is inserted deeply into an inside chamber 25 of solid electrolyte 20.

Solid electrolyte 20 is dipped into chemical plating liquid 80 stored in plating tank 89 to introduce chemical plating liquid 80 into inside chamber 25 of solid electrolyte 20 through small holes 94. In this case, as shown in FIG. 8A, the surface level of chemical plating liquid 80 charged into inside chamber 25 becomes substantially the same as the surface level of bulky chemical plating liquid 80 remaining in plating tank 89, because atmospheric pressure is applied evenly at both of the inside and the outside of branch pipe 93.

In this condition, pressurized air is introduced from pump 900 through main pipe 90 to each branch pipe 93. Receiving this pressurized air, the surface level of chemical plating liquid 80 is forcibly lowered and therefore the residual chemical plating liquid 80 is discharged or returned from inside chamber 25 of each solid electrolyte 20 through small holes 94 to plating tank 89.

Thereafter, upon removal of the pressurized air, surface level of chemical plating liquid 80 is raised and equalized with the surface level of the bulky chemical plating liquid 80 in the plating tank 89, as shown in FIG. 8A. Hence, chemical plating liquid 80 is again introduced into inside chamber 25 of solid electrolyte 20 through small holes 94.

By repeating the above-described operations, chemical plating liquid 80 is circulated in a reciprocative manner between inside chamber 25 of solid electrolyte 20 and plating tank 89. Accordingly, stagnation of chemical plating liquid 80 in inside chamber 25 of solid electrolyte 20 is surely prevented. And, the external electrode and the internal electrode, each having a uniform thickness, are formed on the outer and inner side surfaces of solid electrolyte 20.

However, a recent trend is that relatively smaller oxygen concentration detector elements have been widely used. Therefore, the space available for the inside chamber of the solid electrolyte has been becoming small and narrow. In this respect, the above-described conventional electrode forming method will encounter the following problems.

In forming the internal electrode, injection needle 91 is inserted and left in inside chamber 25. Therefore, the clearance between the wall of inside chamber 25 and injection needle 91 is so narrowed that air bubbles are generated during the plating operation and are settled or trapped in this narrowed space. In other words, the trapped bubble cannot escape from inside chamber 25. For this reason, there is the possibility that plating unevenness may be caused in the formation of the internal electrode.

Furthermore, due to the narrowed space formed between the wall of inside chamber 25 and injection needle 91, circulation of chemical plating liquid 80 into or out of inside chamber 25 is worsened and becomes insufficient. Hence, the plating speed of the inside surface of solid electrolyte 20 is differentiated from and slower than that of the outside surface thereof. As a result, the thickness of the internal electrode resultant through the above-described plating operation becomes small compared with the thickness of the external electrode.

This kind of unevenness in the plating operation of the internal electrode will result in the deterioration of heat-resisting property of the internal electrode. Especially, for an oxygen concentration detector element having an arrangement in which a heater is accommodated in its inside chamber, such deterioration of heat-resisting property will be a serious problem.

SUMMARY OF THE INVENTION

Accordingly, in view of above-described problems encountered in the related art, a principal object of the present invention is to provide a novel and excellent manufacturing method of oxygen concentration detector elements which can assure the stable formation of both the external electrode and the internal electrode with intended thicknesses and flush surfaces free from plating unevenness.

In order to accomplish this and other related objects, a first aspect of the present invention provides a method for manufacturing an oxygen concentration detector element which includes a cup-shaped solid electrolyte with an inside chamber opened at one end and closed at the other end, comprising: an injecting step of inserting an injection needle into the inside chamber of the cup-shaped solid electrolyte and introducing chemical plating liquid into the inside chamber via the injection needle, and then pulling the injection needle out of the inside chamber; a plating step of forming an internal electrode on an inner surface of the inside chamber of the solid electrolyte using the chemical plating liquid; and a discharging step of discharging residual chemical plating liquid from the inside chamber.

According to features of preferred embodiments of the present invention, the injecting step, plating step and discharging step are successively and repeatedly performed.

The solid electrolyte is swung during the plating step. The discharging step is performed by inserting the injection needle into the inside chamber and sucking the residual chemical plating liquid through said injection needle. The internal electrode is made of a single or plurality of substances including at least one selected from the group consisting of Pt, Pd and Rh.

Furthermore, a second aspect of the present invention provides a method for manufacturing an oxygen concentration detector element which includes a cup-shaped solid electrolyte with an inside chamber opened at one end and closed at the other end, the method comprising a plating procedure of forming an external electrode on an outer surface of the solid electrolyte by dipping the solid electrolyte in first chemical plating liquid and forming an internal electrode on an inner surface of the solid electrolyte by introducing second chemical plating liquid into the inside chamber, wherein the plating procedure comprises: an injecting step of inserting an injection needle into the inside chamber of the cup-shaped solid electrolyte and introducing the second chemical plating liquid into the inside chamber via the injection needle, and then pulling the injection needle out of the inside chamber; a plating step of forming the internal electrode on the inner surface of the inside chamber of the solid electrolyte using the second chemical plating liquid; and a discharging step of discharging residual second chemical plating liquid from the inside chamber.

According to the preferred embodiments of the present invention, a pipe is connected to an upper portion of the outer surface of the solid electrolyte, and an upper end of the pipe is positioned higher than a surface level of the first chemical plating liquid, and the second chemical plating liquid is introduced into the inside chamber and the pipe. And also, it is preferable that the first chemical plating liquid is isolated from the second chemical plating liquid during the plating step.

Like the above-described first aspect of the present invention, it is preferable that the discharging step is performed by inserting the injection needle into the inside chamber and sucking the residual second chemical plating liquid through the injection needle. The solid electrolyte is swung during the plating step. The external electrode and the internal electrode are made of a single or plurality of substances including at least one selected from the group consisting of Pt, Pd and Rh. The injecting step, plating step and discharging step are successively and repeatedly performed.

BRIEF DESCRIPTION OF THE DRAWINGS

The above and other objects, features and advantages of the present invention will become more apparent from the following detailed description which is to be read in conjunction with the accompanying drawings, in which:

FIGS. 7A, 7B and 7C are views illustrating another plating method of forming an external electrode and an internal electrode of the oxygen concentration detector element in accordance with a second embodiment of the present invention;

DETAILED DESCRIPTION OF THE PREFERRED EMBODIMENTS

Figure 1:
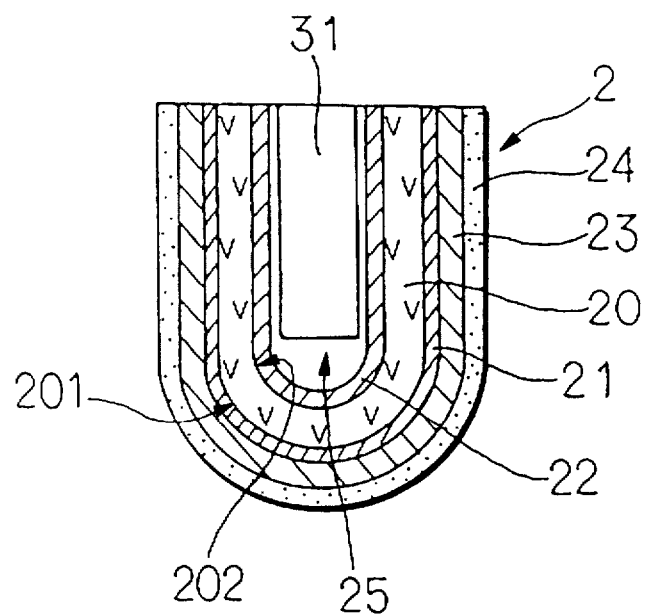
FIG. 1 is a cross-sectional view showing an essential part of an oxygen concentration detector element in accordance with a first embodiment of the present invention.

Preferred embodiments of the present invention will be explained in greater detail hereinafter with reference to the accompanying drawings. Identical parts are denoted by the same reference numerals throughout the views.

A method of manufacturing an oxygen concentration detector element in accordance with the present invention will be explained with reference to a first embodiment shown in FIGS. 1 to 6.

As shown in FIG. 1, the first embodiment uses an oxygen concentration detector element 2 capable of causing an electromotive force in accordance with rich and lean of oxygen concentration, which is preferably used to detect the oxygen concentration of exhaust gas emitted from an automotive vehicle.

Figure 2:
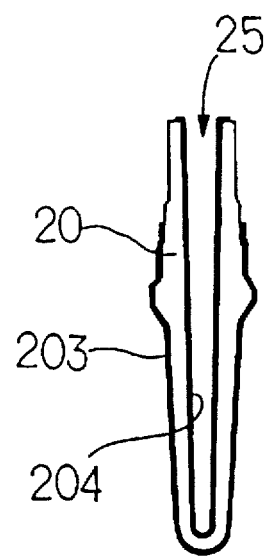
FIG. 2 is a schematic cross-sectional view showing the oxygen concentration detector element in accordance with the first embodiment of the present invention.

As shown in FIGS. 1 and 2, oxygen concentration detector element 2 comprises a cup-shaped solid electrolyte 20 having an inside chamber 25 with one end closed and the other end opened. Solid electrolyte 20 has an outer surface 201. An external electrode 21 is formed by applying chemical plating so as to extend in a predetermined region 203 of this outer surface 201.

On the other hand, solid electrolyte 20 has an inner surface 202. An internal electrode 22 is formed by applying chemical plating so as to extend in a predetermined region 204 of this inner surface 202.

Furthermore, an electrode protecting layer 23 covering external electrode 21 and a trapping layer 24 are successively provided on the surface of the external electrode 21. Trapping layer 24 is made of a porous body of $\gamma$-$Al_2O_3$. Electrode protecting layer 23 is formed by plasma spraying $MgO.Al_2O_3$ spinel or the like material which has a capability of protecting electrodes as well as a function of controlling the diffusion of oxygen ions. The material used for forming the external electrode 21 and internal electrode 22 is platinum (Pt) in this embodiment. Palladium (Pd) or rhodium (Rh) can also be used as the material of external electrode 21 and internal electrode 22.

Figure 3:
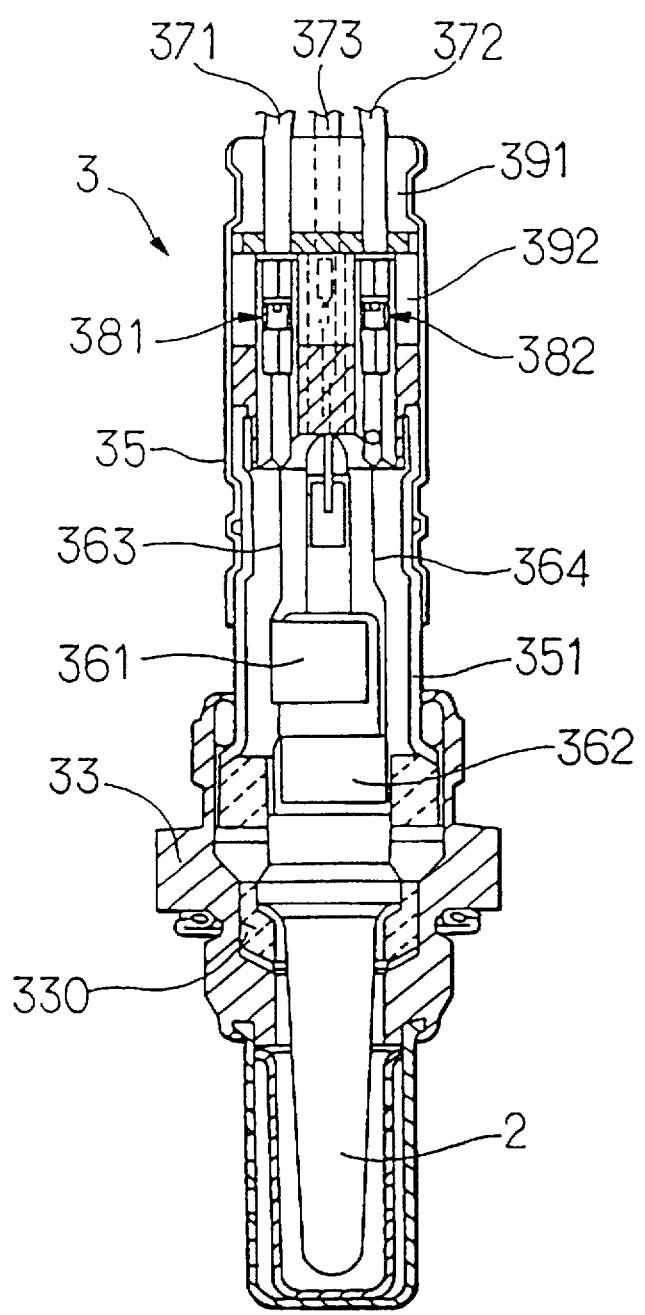
FIG. 3 is a cross-sectional view showing a detailed arrangement of an oxygen concentration detector in accordance with the first embodiment of the present invention.
Figure 4:
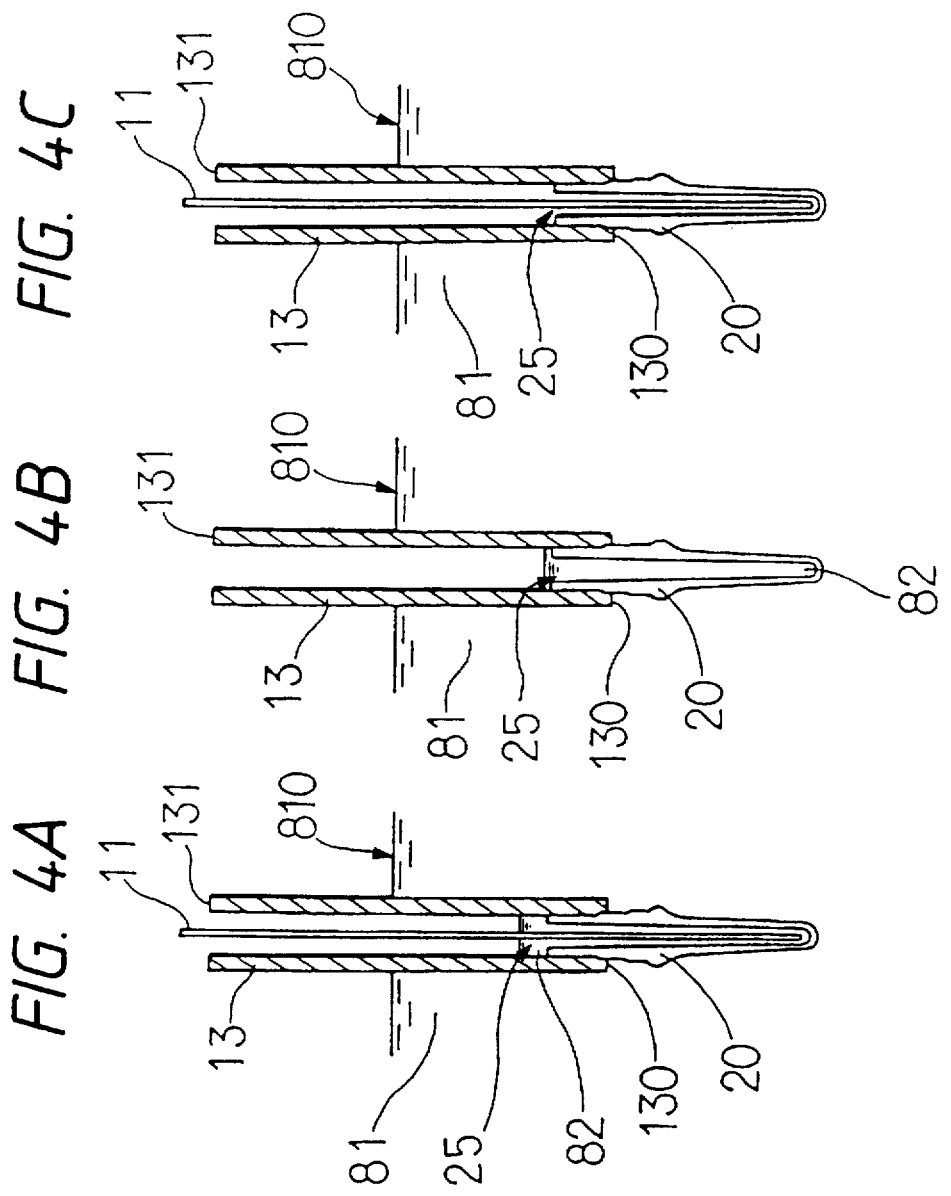
FIGS. 4A, 4B and 4C are views illustrating a plating procedure for forming an external electrode and an internal electrode of the oxygen concentration detector element in accordance with the first embodiment of the present invention.

As shown in FIG. 3, oxygen concentration detector element 2 is securely coupled with the front (lower) end portion of an oxygen concentration detector 3. More specifically, oxygen concentration detector element 2 is fixed to a cylindrical metal housing 33 through an insulating member 330.

A main body cover 351, at its lower end portion, is securely engaged with the metal housing 33 so as to close the opening of metal housing 33. A connector cover 35 is coupled with the upper end portion of main body cover 351 so as to accommodate insulating members 391 and 392 therein.

Disposed in the insulating member 391 are a pair of lead lines 371 and 372 which take out electric detection signals and a single lead line 373 which supplies electric power to a heater 31 disposed in the inside chamber 25.

Lead lines 371 and 372 are electrically connected to external electrode 21 and internal electrode 22 respectively via connectors 381 and 382, electrode lead lines 363 and 364, and board terminals 361 and 362.

Next, a method of manufacturing the above-described oxygen concentration detector element 2 will be explained.

First, outer surface 201 and inner surface 202 of electrolyte 20 are subjected to chemical etching using strong acid such as hydrofluoric acid.

Next, as shown in FIG. 2, an activation process (deposition of platinum) is applied on external electrode forming region 203 and internal electrode forming region 204 on solid electrolyte 20. Regarding this activation processing, it is possible to deposit platinum by exposing the surface of solid electrolyte 20 to a solution of platinum chloride acid and a solution of sodium boron hydride.

Next, external electrode 21 and internal electrode 22 are formed by applying chemical plating which will be later described in detail. Thereafter, a thermal processing is applied on the external electrode 21 and internal electrode 22.

Subsequently, plasma spraying of $MgO.Al_2O_3$ spinel or the like material is applied on the surface of external electrode 21 to form the protecting layer 23. Furthermore, $\gamma\text{-}Al_2O_3$ particles are attached on the surface of this protecting layer 23 by dipping, and then baked to form the trapping layer 24 on the protecting layer 23, thereby finally obtaining the oxygen concentration detector element 2 shown in FIG. 1.

Next, with reference to FIGS. 4A, 4B, 4C, 5 and 6, the details of a method of forming external electrode 21 and internal electrode 22 performed under a condition in which solid electrolyte 20 is supported by a pipe 13 will be explained.

Figure 5:
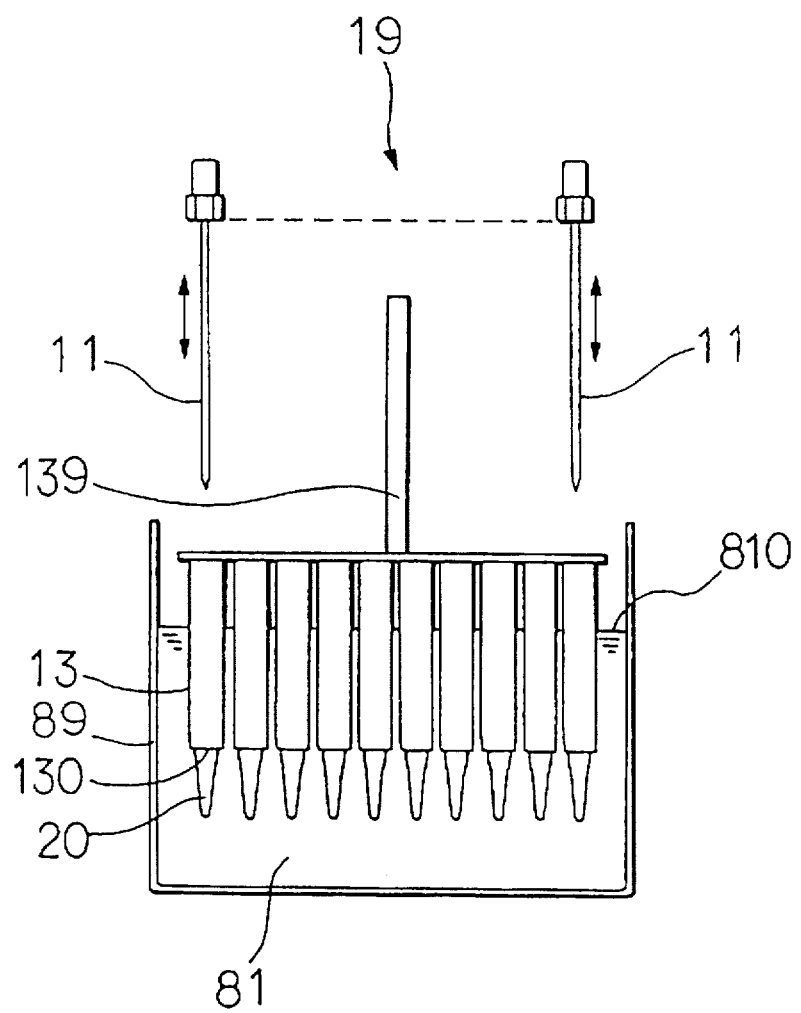
FIG. 5 is a schematic view showing a plating tank and a plating jig used in the first embodiment of the present invention.

As shown in FIG. 5, to form the internal electrode 22 and external electrode 21 on the solid electrolyte 20, this embodiment uses a plating tank 89 storing first chemical plating liquid 81 therein and a plating jig 19 associated with this plating tank 89.

Plating jig 19 comprises numerous pipes 13 extending downward from a horizontal handling bar 139, so that injection needle 11 can be inserted into and extracted from the inside space of pipe 13. Injection needle 11 is not fixed to pipe 13 and, therefore, can be moved freely in the up-and-down direction.

Furthermore, pipe 13 is made of rubber and, as shown in FIG. 4A, the lower end of pipe 13 is coupled and firmly engaged with the upper part of outer surface 201 of solid electrolyte 20 using the resilient force of rubber. After that, solid electrolyte 20 is dipped into first chemical plating liquid 81 in the plating tank 89, so that the external electrode forming region 203 can be surely placed lower than the surface level 810 of first chemical plating liquid 81. The upper end 131 of pipe 13 is positioned higher than the surface level of first chemical plating liquid 81.

Next, as shown in FIG. 4A, injection needle 11 is inserted into pipe 13 until it enters the inside chamber 25 of solid electrolyte 20. Then, second chemical plating liquid 82 is introduced into inside chamber 25 through injection needle 11. In this case, the injection amount of second chemical plating liquid 82 is large enough to be also introduced into the inside space of pipe 13. Thereafter, injection needle 11 is quickly pulled out of inside chamber 25 and pipe 13, thus accomplishing an injecting or filling process.

Next, as shown in FIG. 4B, solid electrolyte 20 is left for 30 minutes to deposit external electrode 21 made from first chemical plating liquid 81 on the outer surface thereof and internal electrode 22 made from second chemical plating liquid 82 on the inner surface thereof, thereby accomplishing a plating process.

Then, as shown in FIG. 4C, injection needle 11 is again inserted into inside chamber 25 to suck residual second chemical plating liquid 82 out of inside chamber 25, thus completing a discharging process.

In this manner, the injecting process, plating process and discharging process are sequentially performed and repeated until the thickness of internal electrode 22 becomes a desired value. When the above-described plating operation is finished, solid electrolyte 20 is lifted out of first chemical plating liquid 81.

In this embodiment, the composition of first chemical plating liquid 81 is identical with the composition of second chemical plating liquid 82. However, the composition of first chemical plating liquid 81 can be differentiated from that of second chemical plating liquid 82.

Function and effect of the first embodiment will be explained hereinafter.

According to this embodiment, inside chamber 25 can be isolated from first chemical plating liquid 81 during the formation of external electrode 21. Therefore, it becomes possible to use the second chemical plating liquid 82 to form the internal electrode 22.

Accordingly, the thickness of internal electrode 22 can be determined independent of the thickness of external electrode 21.

Furthermore, in the formation of internal electrode 22, injection needle 11 is pulled out of the inside chamber 25 after finishing the injecting process. Therefore, it becomes possible to eliminate the possibility of causing the unevenness in the plating thickness due to the presence of injection needle 11 in the succeeding plating process.

Furthermore, in the forming process of the internal electrode, the injecting process, the plating process and the discharging process are successively repeated to obtain internal electrode 22 having a desirable thickness.

Still further, as the second chemical plating liquid 82 is injected in pipe 13, it becomes possible to form the internal electrode 22 at the periphery of the upper opening of inside chamber 25 as well as the wall of inside chamber 25 of solid electrolyte 20. It is also possible to increase the amount of second chemical plating liquid 82 to be used in each plating process.

Yet further, in the plating process other than the injecting process and the discharging process, solid electrolyte 20 is swung (or agitated) adequately. With this swinging motion, it becomes possible to always and smoothly supply fresh first chemical plating liquid 81 and second chemical plating liquid 82 to the outer surface 201 and inner surface 202 of solid electrolyte 20. If an bubble is accidentally caused, such an air bubble will be easily removed from the surface of solid electrolyte 20 by the function of this swinging motion without giving any adverse effect to the plating reaction.

Accordingly, by adding the above-described swing motion to solid electrolyte 20, not only is the reaction speed increased in the plating process, but also the plating surface is uniformly formed. In other words, external electrode 21 and internal electrode 22 each having a uniform thickness can be formed within a relatively short time.

Hence, the first embodiment of the present invention can provide a novel and excellent manufacturing method for oxygen concentration detector elements according to which the external electrode and the internal electrode are surely and stably formed so as to have a required thickness and a flush surface.

Moreover, the lower end portion of pipe 13 does not need to be dipped into the first chemical plating liquid 81 when the external electrode forming region 23 is limited to the front (lower) end portion of the solid electrolyte 20.

Figure 6:
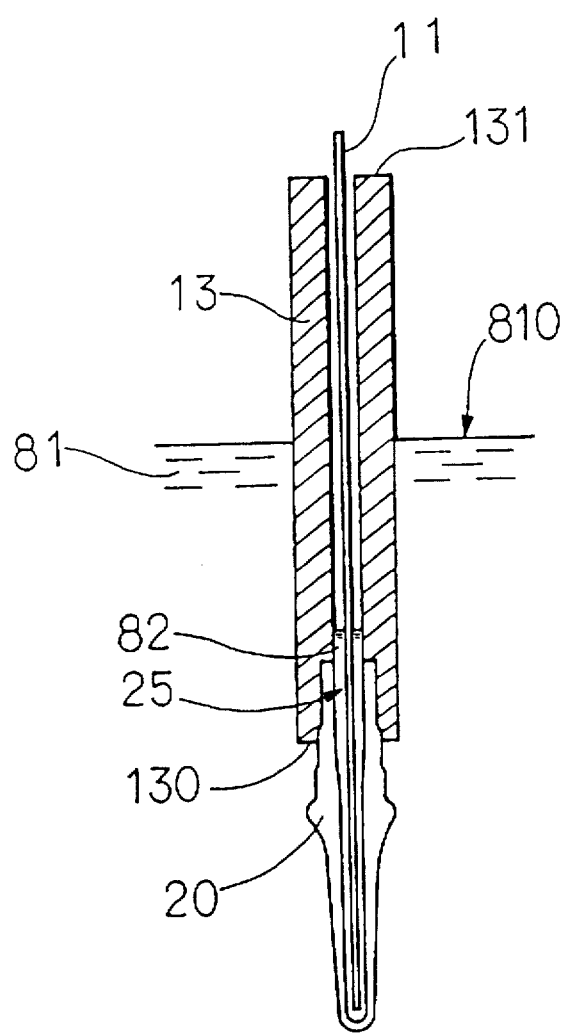
FIG. 6 is a cross-sectional view showing a modification of the formation of the external and internal electrodes of the oxygen concentration detector element in accordance with the first embodiment of the present invention.
Figure 8A:
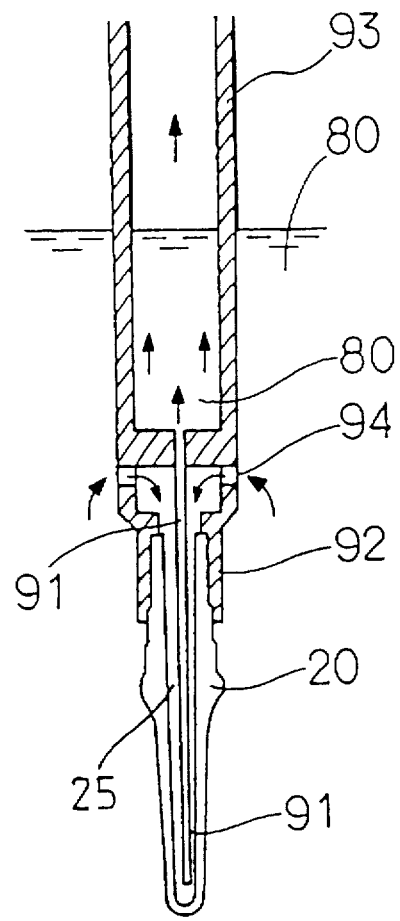
FIGS. 8A and 8B are views showing a conventional plating method of forming external and internal electrodes of the oxygen concentration detector element.
Figure 8B:
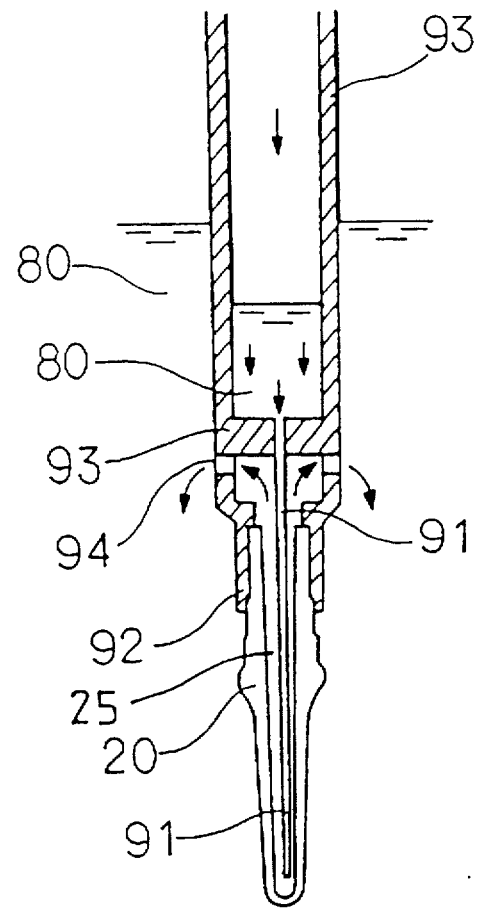

Furthermore, it is also possible to adopt an arrangement that forms no electrode on the periphery of the upper opening of solid electrolyte 20 as shown in FIG. 6.

Hereinafter, a second embodiment of the present invention will be explained, with reference to FIGS. 7A to 7C. The second embodiment disclose a manufacturing method of oxygen concentration detector elements which forms the external electrode and the internal electrode without using pipe 13.

First, solid electrolyte 20 is securely fixed to a holder (plating jig) 19. Then, solid electrolyte 20 is dipped into first chemical plating liquid 81 in the plating tank in the same manner as in the first embodiment. In this case, the level of upper opening periphery 250 of solid electrolyte 20 is set higher than the surface level 810 of first chemical plating liquid 81.

Next, as shown in FIG. 7A, injection needle 11 is inserted into the inside chamber 25 of solid electrolyte 20. Then, second chemical plating liquid 82 is introduced into the inside chamber 25, without causing the second chemical plating liquid 82 to overflow into the first chemical plating liquid 81. Then, injection needle 11 is pulled out of the inside chamber 25. (Injecting process)

Then, as shown in FIG. 7B, after injection needle 11 is pulled out of the inside chamber 25, the solid electrolyte 20 is left stationarily for a predetermined time in this condition to deposit electrodes thereon. Thus, external electrode 21 is made from first chemical plating liquid 81 while internal electrode 22 is made from second chemical plating liquid 82. (Plating process)

Subsequently, as shown in FIG. 7C, injection needle 11 is again inserted into the inside chamber 25 to suck the residual second chemical plating liquid 82 out of the inside chamber 25. (Discharging process)

In this second embodiment, no swing motion is given to solid electrolyte 20.

According to the above-described method of forming external electrode 21 and internal electrode 22, desirable and excellent effect (i.e. attaining a uniform plating operation, and gaining a desirable thickness and a flush surface) similar to the first embodiment can be obtained in the formation of the electrodes on the solid electrolyte.

Tables 1 and 2 cooperatively show comparative results with respect to the formation of the external electrode and the internal electrode between the present invention and the prior art. Samples 1 to 3 relate to the present invention which are formed according to the method of the first embodiment shown in FIGS. 4 and 5. A total of 100 solid electrolytes are used to demonstrate the formation of the external electrode and the internal electrode in each of the samples 1 to 3.

Regarding the first chemical plating liquid in samples 1 and 2, a mg of platinum is charged into the first chemical plating liquid to form the external electrode with a thickness of 1 μm when the plating adhesion efficiency is 90%. Regarding sample 3, 1.5a mg of platinum is charged into the first chemical plating liquid to form the external electrode with change a thickness of 1.5 μm when the plating adhesion efficiency is 90%.

Meanwhile, regarding the second chemical plating liquid in each of samples 1 to 3, platinum of b mg is charged into the second chemical plating liquid to form the internal electrode with a thickness of 1 μm when the plating adhesion efficiency is 90%.

In the formation of samples 1 and 3, the solid electrolyte is swung during the plating process of the external and internal electrodes. On the other hand, in the formation of sample 2, no swing motion is given to the solid electrolyte.

A continuation time of 5 hours is required to accomplish the external electrode forming process, as shown in Table 1. The internal electrode forming process consists of three processes described in the first embodiment; i.e., the injecting process, plating process, and discharging process. The internal electrode forming process takes 45 minutes to thoroughly perform, and has been done 6 times repeatedly. In short, as shown in Table 1, a total continuation time spent for forming the internal electrode amounts to 4.5 hours.

Figure 9:
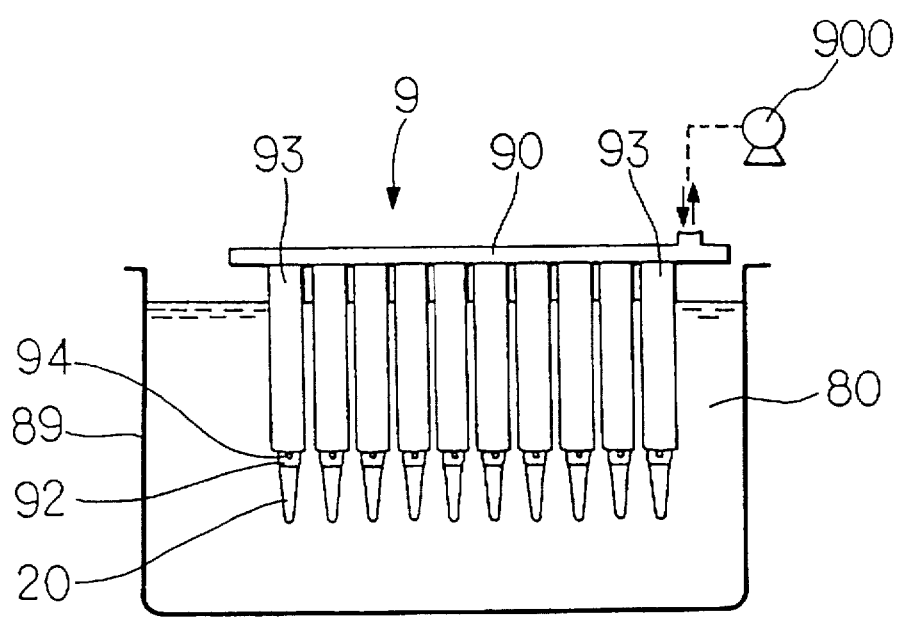
FIG. 9 is a schematic view showing a plating tank and a plating jig used in the conventional plating method.

Comparative sample C1 relates to the prior art technique which is formed according to the conventional method shown in FIG. 9. A total of 100 solid electrolytes are used to demonstrate the formation of the external electrode and the internal electrode in accordance with the conventional method.

As shown in Table 2, in this comparative example C1, platinum of a+b mg is charged into the chemical plating liquid to form both the external and internal electrodes. Ten hours is required to accomplish the plating process according to the conventional method.

Hereinafter, a method for evaluating the present invention samples 1 to 3 and the comparative sample C1 will be explained.

Of 100 samples in each of samples 1 to 3 and comparative sample C1, a total of 20 samples are selected at random. In each of the selected samples, the thickness of the external and internal electrodes is measured by using fluorescent X-ray film thickness gauge at four points angularly spaced 90° in a circumferential direction at the height 5 mm downward from the upper opening periphery of each solid electrolyte.

Average or mean values derived from the measurements and their dispersions (standard deviations) are shown in Tables 1 and 2.

Furthermore, all the samples were broken to check how the internal electrode has a glossy surface. If a sample is regarded through a visual monitoring as having any portion poor in gloss, is judged to be defective because of unevenness of plating. Tables 1 and 2 show the total number of these defective samples among 100 samples.

As shown in Tables 1 and 2, it is recognized that the samples 1 to 3 of the present invention are satisfactory in obtaining a uniform thickness in the formation of the external and internal electrodes. Dispersion of the resultant thickness was very small. It is found in each of samples 1 to 3 that no plating unevenness is caused on the internal electrode.

On the contrary, in the comparative example C1, it is found that the external electrode is formed thicker than the internal electrode. Dispersion of the resultant thickness was large. Furthermore, of 100 samples, a total of 35 defective samples were detected as having plating unevenness. In other words, the percentage of defective samples exceeds ⅓.

In the comparison between sample 1 and sample 2 of the present invention, it is found that applying the swing motion to the solid electrolyte is effective to increase the plating adhesion efficiency. Namely, the thickness of the resultant external and internal electrodes in the sample 2 is slightly thinner compared with that of the sample 1.

TABLE 1

|  | Sample 1 | Sample 2 | Sample 3 |
|---|---|---|---|
| Plating condition I:<br>Pt charge amount in 1st chemical plating liquid (μg) | a | a | 1.5a |
| Plating condition II:<br>Pt charge amount in 2nd chemical plating liquid (mg) | b | b | b |
| Plating condition III:<br>Adoption of swing motion | Yes | No | Yes |
| Plating condition IV:<br>Continuation time for forming external electrode (hr) | 5 | 5 | 5 |
| Plating condition V:<br>Continution time for forming internal electrode (hr) | 4.5 | 4.5 | 4.5 |
| Plating adhesion efficiency (%) | 90 | 85 | 90 |
| External electrode: Means thickness (μm) | 1.00 | 0.95 | 1.50 |
| External electrode: Dispersion | 0.02 | 0.04 | 0.02 |
| Internal electrode: Mean thickness (μm) | 1.00 | 0.98 | 1.00 |
| Internal electrode: dispersion | 0.02 | 0.03 | 0.02 |
| Presence of plating unevenness | 0/100 | 0/100 | 0/100 |

|  | Sample C1 |
|---|---|
| Plating condition I:<br>Pt charge amount in chemical plating liquid (mg) | a + b |
| Plating condition II:<br>Aeration | Yes |
| Plating condition III:<br>Plating time (hr) | 10 |
| Plating adhesion efficiency (%) | 90 |
| External electrode: Means thickness (μm) | 1.09 |
| External electrode: Dispersion | 0.05 |
| Internal electrode: Mean thickness (μm) | 0.87 |
| Internal electrode: dispersion | 0.08 |
| Presence of plating unevenness | 35/100 |

As apparent from the foregoing description, the present invention provides a manufacturing method for oxygen concentration detector elements which can assure the stable formation of both the external electrode and the internal electrode with intended thicknesses and flush surfaces.

As this invention may be embodied in several forms without departing from the spirit of essential characteristics thereof, the present embodiments described are therefore intended to be only illustrative and not restrictive, since the scope of the invention is defined by the appended claims rather than by the description preceding them, and all changes that fall within the metes and bounds of the claims, or equivalents of such metes and bounds, are therefore intended to be embraced by the claims.

What is claimed is:

1. A method for manufacturing an oxygen concentration detector element which includes a cup-shaped solid electrolyte with an inside chamber opened at one end and closed at the other end, said method comprising the steps of:

forming an external electrode on an outer surface of said solid electrolyte by dipping said solid electrolyte in first chemical plating liquid; and forming an internal electrode on an inner surface of said solid electrode by inserting an injection needle into said inside chamber of said cup-shaped solid electrolyte and injecting a second chemical plating liquid into said inside chamber via said injection needle, said second chemical plating liquid being isolated from said first chemical plating liquid, then pulling said injection needle out of said inside chamber electrolessly plating the internal electrode on the inner surface of said solid electrolyte using said second chemical plating liquid, and then discharging residual second chemical plating liquid from said inside chamber after said internal electrode is formed on the inner surface of said solid electrolyte.

2. The manufacturing method in accordance with claim 1, wherein said discharging step is performed by inserting said injection needle into said inside chamber and sucking said residual second chemical plating liquid through said injection needle.

3. The manufacturing method in accordance with claim 1, wherein a pipe is connected to an upper portion of the outer surface of said solid electrolyte, and an upper end of said pipe is positioned higher than a surface level of said first chemical plating liquid, and said second chemical plating liquid is supplied into said inside chamber and said pipe.

4. The manufacturing method in accordance with claim 1, wherein said solid electrolyte is swung during said plating step.

5. The manufacturing method in accordance with claim 1, wherein said external electrode and said internal electrode are made of a single or plurality of substances including at least one selected from the group consisting of platinum, palladium and rhodium.

6. The manufacturing method in accordance with claim 1, wherein said injecting step, plating step and discharging step are successively and repeatedly performed.

* * * * *